United States Patent [19]

Cole

[11] Patent Number: 5,009,224

[45] Date of Patent: Apr. 23, 1991

[54] METHOD FOR ATTACHING A PRESSURE-SENSITIVE FILM ARTICLE HAVING HIGH MOISTURE VAPOR TRANSMISSION RATE

[75] Inventor: Susan M. Cole, St. Paul, Minn.

[73] Assignee: Minnesota Mining and Manufacturing Company, St. Paul, Minn.

[21] Appl. No.: 561,247

[22] Filed: Jul. 30, 1990

Related U.S. Application Data

[63] Continuation of Ser. No. 266,201, Oct. 27, 1988, abandoned, which is a continuation of Ser. No. 913,688, Sep. 30, 1986, abandoned.

[51] Int. Cl.$^5$ .............. A61F 13/00; A61F 15/00; A61L 15/00
[52] U.S. Cl. ................. 128/156; 128/887; 604/307; 604/336; 523/111; 428/315.5
[58] Field of Search ............ 128/156, 887; 604/307, 604/332, 336; 523/111; 428/315.5, 317.3, 317.7, 345, 351, 423.7

[56] References Cited

U.S. PATENT DOCUMENTS

| | | |
|---|---|---|
| 3,645,835 | 2/1972 | Hodgson ................. 161/146 |
| 3,972,328 | 8/1976 | Chen ........................ 128/156 |
| 4,181,752 | 1/1980 | Martens et al. ............ 427/54.1 |
| 4,415,615 | 11/1983 | Esmay et al. ............ 428/317.5 X |
| 4,427,737 | 1/1984 | Cilento et al. ........... 428/317.5 X |
| 4,452,845 | 6/1984 | Lloyd et al. .............. 128/156 X |
| 4,499,896 | 2/1985 | Heinecke .................. 128/156 |
| 4,513,739 | 4/1985 | Johns ....................... 128/156 |
| 4,554,317 | 11/1985 | Behar et al. ............. 128/156 X |
| 4,559,938 | 12/1985 | Metcalfe .................. 128/156 |
| 4,598,004 | 7/1986 | Heinecke .................. 428/40 |
| 4,773,409 | 9/1988 | Cilento et al. ............ 128/156 |

FOREIGN PATENT DOCUMENTS 1192825  9/1985  Canada ..................... 154/86
83/03549 10/1983 World Int. Prop. O. .

*Primary Examiner*—Randall L. Green
*Assistant Examiner*—Paul Prebilic
*Attorney, Agent, or Firm*—D. M. Sell; C. A. Bates

[57] ABSTRACT

A method is disclosed for treating a wound or attaching a device or article to the skin using a film of pressure sensitive adhesive having dispersed therein a discontinuous gaseous phase contained within voids in the adhesive. The adhesive is formed from the polymerization of a hydrophilic premix and exhibits high moisture vapor transmission and fluid absorbency.

23 Claims, No Drawings

METHOD FOR ATTACHING A PRESSURE-SENSITIVE FILM ARTICLE HAVING HIGH MOISTURE VAPOR TRANSMISSION RATE

This is a continuation of application Ser. No. 07/266,201 filed Oct. 27, 1988 now abandoned, which is a continuation of Ser. No. 913,688, filed Sept. 30, 1986 now abandoned.

FIELD OF THE INVENTION

This invention relates to a pressure-sensitive adhesive film article. In particular, this invention relates to an article comprising a film of pressure-sensitive adhesive, which article is useful in the moist healing of wounds.

BACKGROUND OF THE INVENTION

In recent years, the technique of wound repair known as moist healing has become well established. It is an improvement in many cases over the traditional method of letting a wound dry out, forming a scab or crust over the surface, followed by regrowth of tissue underneath the scab. It has been found that, relative to dry healing, moist healing often results in cleaner repair, with less scarring and less pain to the patient than dry healing, especially when the wound is an extensive burn or large abrasion. Dressings for moist healing therapy are frequently made of thin films of synthetic polymers such as polyurethanes as described in U.S. Pat. No. 3,645,835. One of the characteristics of these films is their ability to selectively allow water molecules ("moisture vapor") to pass through them while preventing the passage of liquid water or aqueous solutions and, most importantly, bacteria. By careful selection of film and adhesive, a dressing can be provided which keeps a wound moist and sterile, but which allows excess liquid to evaporate. It also conforms well to the skin, and is unobtrusive in use.

Such dressings, however, have several disadvantages when used with certain kinds of wounds. When a wound is seeping copiously the "moisture vapor transmission" (MVT) capability of the film cannot remove excess liquid fast enough. As a result, fluid may accumulate under the dressing which can result in skin maceration. In practice, a film of sufficiently high MVT to be useful as a dressing on highly exudative wounds would have to be too thin to be practical. Even film dressings in commercial use today are so thin and flimsy that they are extremely difficult to apply without special delivery means such as those described in U.S. Pat. Nos. 4,513,739, 4,598,004 and Canadian Patent No. 1,192,825.

The problem of handling copiously-seeping wounds was addressed in U.S. Pat. No. 4,499,896 by providing a reservoir dressing with one or more extra layers of thin film, sealed together at their peripheries, to form pouches into which excess liquid can flow temporarily. These pouches or reservoirs have additional surface area through which moisture evaporation can take place. These dressings have found utility, but are clearly more complicated and costly than dressings made from a single film.

Another disadvantage of conventional thin film dressings is that they provide very little mechanical cushioning to a wound. Wound protection against bumps and scrapes is not addressed by these thin dressings.

Foam backings for wound dressings are known (e.g. Microfoam TM brand surgical tape, 3M Co.) where the foam provides a thicker, more conformable, more cushioning material than would be provided by the same weight of unfoamed backing. The backing of Microfoam TM brand surgical tape is open cell polyvinylchloride which is not a barrier for micro organisims. If the polyvinylchloride was made with closed cells, it would not have a sufficiently high MVT for moist wound healing without skin maceration.

U.S. Pat. No. 4,559,938 (Metcalfe) discloses an adhesive dressing comprised of a backing and a conventional pressure-sensitive adhesive. The backing is a film formed from a blend of a continuous matrix of 1,2-polybutadiene and an incompatible polymer which forms a discrete particulate phase within the matrix. This film is stretched to introduce a plurality of small, preferably closed, voids in the film which nominally enhance the moisture vapor permeability of the film. It is believed that the moisture vapor permeability of the dressing (through film and adhesive) is too low to be used in moist wound healing without skin maceration.

Thus, there exists a need for a wound dressing which provides controlled transmission and/or absorption of water vapor away from a wound so that the wound remains moist but not excessively so, and which is also thick and flexible enough to alleviate the need for elaborate delivery means and to provide mechanical cushioning of a wound.

SUMMARY OF THE INVENTION

According to the present invention, there is provided a pressure-sensitive adhesive article for use on skin comprising a continuous film of pressure-sensitive adhesive having dispersed therein a discontinuous gaseous phase contained within voids within said film, which gaseous phase constitutes at least 10 percent of the volume of said pressure-sensitive adhesive. The film has a moisture vapor transmission and absorbency sufficient to permit moist healing of wounded skin without skin maceration, e.g., an MVT of at least about 400 $g/m^2$ per 24 hours measured at 40° C. and 80% relative humidity differential.

The adhesive film of the invention has cellular voids containing a gaseous phase to effect control of adhesive thickness and to provide a multiplicity of microreservoirs or micropouches. The film allows water vapor to pass at a controlled rate by diffusion of water vapor through the adhesive surrounding the voids and collection of water vapor in the voids, but prevents liquid media (e.g., water) and bacteria from traversing the film. This controlled diffusion of water vapor allows for the presence of an optimal amount of moisture at the site of a healing wound covered by the film. The cellular construction of the film also provides mechanical cushioning of the wound.

In a preferred embodiment of the adhesive article of the invention, a film of cellular pressure-sensitive adhesive is in contact with one face of a conformable sheet. The conformable sheet preferably has high moisture vapor transmission i.e., at least about 1000 $g/m^2$ per 24 hrs at 40° C. and 80% humidity differential.

Another aspect of this invention relates to a method of preparing a pressure-sensitive adhesive article as described above comprising:

(a) forming a hydrophilic polymerizable composition which polymerizes to a pressure-sensitive adhesive state;

(b) foaming said composition;

(c) coating a carrier with said foamed composition; and (d) polymerizing said coating to a pressure-sensitive adhesive state.

The hydrophilicity of the polymerizable composition may be provided by the inclusion of: (1) a hydrophilic, ethylenically unsaturated monomer, e.g., acrylic acid or an acrylate or acrylamide terminated polyether; (2) by a hydrophilic additive, e.g., a polyhydric polyol, or polyether; or (3) both a hydrophilic monomer and a hydrophilic additive. The degree of hydrophilicity required of the polymerizable composition is that degree which is sufficient to provide a pressure-sensitive adhesive having the desired degree of moisture vapor transmission.

DETAILED DESCRIPTION

The pressure-sensitive adhesive films of this invention must have a sufficiently high moisture vapor transmission and absorbency to permit moist healing of a wound without skin maceration. Moist healing is the retention at a wound of an optimum amount of moisture which (1) prevents the formation of a scab, (2) increases the rate of epithelial cell migration, and (3) does not allow pooling of moisture or wound exudate. Skin maceration is a deleterious effect of pooling of excess liquid, e.g., water or bodily fluid, on the normal skin surrounding a wound. Skin maceration is indicated by whitening and softening of the affected skin. In general, adhesive films of this invention having a moisture vapor transmission of at least about 400 g/m$^2$ per 24 hrs measured at 40° C. and 80% relative humidity differential are sufficiently absorptive and transmissive to avoid skin maceration and promote moist wound healing. The moisture vapor transmission is preferably at least about 500 g/m$^2$ per 24 hrs., and most preferably from about 600 to about 2400 g/m$^2$ per 24 hrs. The adhesive film useful in this invention is cellular, i.e., non-porous, such that it possesses substantially total impermeability to liquid water and bacteria.

Moisture vapor transmission as referred to herein and in the claims, except as otherwise noted, refers to moisture vapor permeability determined in accordance with the test described below. Impermeable to liquid water as used herein means impermeable to liquid water as indicated by the dye penetration test described below.

The adhesive film is rendered moisture vapor permeable and absorbent by the hydrophilicity of the adhesive composition and the cellular voids in the film. The thickness of the adhesive film, along with the hydrophilicity and the voids, affects the absorption capacity of the adhesive film. The adhesive film is rendered hydrophilic by the addition of hydrophilizing agents to the polymerizable premix from which the adhesive is prepared such as those described below.

As used herein, "percent void volume" means that portion of the thickness of the cellular adhesive membrane attributable to cellular voids. Percent void volume is conveniently measured by the equation:

$$\% V = \frac{d_u - d_f}{d_u} \times 100$$

wherein $d_u$ is the unfoamed density and $d_f$ is the foamed density of the adhesive. Unfoamed density can be determined from the density of the starting materials or by compressing the foamed adhesive. Adhesive films according to the invention should have void volumes of from about 10 to about 85 percent. The higher the void volume of the adhesive film, the greater the MVT, absorbency, conformability, and cushioning ability of the dressing.

The adhesive films of this invention possess useful absorbency in addition to their ability to transmit water vapor. When the film is composed of an adhesive having low absorbency, the difference in absorbency between the foamed state and the unfoamed is pronounced (See Examples 1–6). This effect is less pronounced in the case of adhesives which are already highly absorbent, but in both cases the end product has the ability to absorb significant quantities of water. The water is not easily removable from the foam by squeezing. This is a useful distinction from conventional reservoir dressings used on highly exudative wounds, wherein the contents of the reservoirs may leak out when the dressing is manipulated.

Also, typical pressure-sensitive adhesive films of the invention have remarkably good flexibility and conformability which are advantageous properties in a wound dressing.

The pressure-sensitive adhesive films of the invention are derived from a hydrophilic polymerizable premix into which cellular voids are introduced. The premix is made hydrophilic by the addition of a hydrophilizing agent such as a hydrophilic, ethylenically unsaturated monomer, a hydrophilic additive or both. Preferred hydrophilic additives are polyhydric alcohols, polyethers, or mixtures thereof. The polyhydric alcohol or polyether is present in the premix in an amount sufficient to raise the moisture vapor transmission of the adhesive to the desired level. This amount ranges, in general, from about 20 to about 85 parts by weight of the premix, with about 30 to about 70 being preferred. Examples of useful polyhydric alcohols and polyethers include glycerin, propylene glycol, polypropylene oxide glycols, polyethylene oxide glycols, 1,2,4-butanetriol, and sorbitol and mixtures thereof. The dihydric alcohol, ethylene glycol is useful in the present invention, but may cause dermal reactions which limit its utility.

The hydrophilizing agent may also have ethylenic unsaturation which will allow it to copolymerize with other free radically polymerizable materials in the premix as described below. For example, a polyether polyol can be terminated with acrylic or methacrylic acid, or a reactive derivative thereof, to yield an acrylate or methacrylate terminated polyether, e.g., poly(oxyethylene)acrylate. Also, an amine terminated polyether can be terminated with acrylic or methacrylic acid, or a reactive derivative thereof, to yield an acrylamide or methacrylamide terminated polyether, e.g, N-poly(oxypropylene)acrylamide.

The premix is also comprised of an unsaturated free radically polymerizable material which when polymerized renders the premix pressure-sensitive adhesive, and which is preferably miscible with the hydrophilizing agent. This material may consist of a single monomer or a mixture of comonomers. These monomers or comonomers are present in the premix in amounts of from about 100 to about 10 parts by weight of the premix preferably from about 50 to about 20. Examples of useful monomers or comonomers are alkyl acrylates having an average of 4–12 carbon atoms in their alkyl groups, acrylic acid, methacrylic acid, and salts thereof, acrylamide, methacrylamide, hydroxyalkylacrylates, hydroxyalkylmethacrylates, acrylonitrile, methacrylonitrile, cyanoethylacrylate, maleic anhydride and N-vinyl pyrrolidone.

It is preferred that the premix contain a plasticizing component which is conveniently provided by the polyether or polyol hydrophilic additive or the polyether- or polyol-containing monomer.

The premix is also preferably comprised of a thickening agent of polymeric material which is preferably soluble in the polymerizable composition. These polymeric materials are present in the premix in amounts of about 0.1 to about 70 parts by weight of the premix. Examples of useful polymeric materials are sodium carboxymethyl cellulose, hydroxyethylcellulose, methoxyethyl cellulose, chitosan, polyvinyl alcohol, polyvinylpyrrolidone, polyacrylic acid, polyvinylethers, copolymers of maleic anhydride and polyvinylethers, starch, hydroxypropyl-cellulose, polyacrylamide, copolymers of alkyl acrylates and acrylic acid or its salts, polyethylenimine, ethylene oxide polymers and propylene oxide polymers.

The adhesive film is preferably crosslinked. One means of crosslinking is the inclusion of a multi-ethylenically unsaturated, free radically polymerizable material, generally in an amount of from about 0.1 to about 5 parts by weight per 100 parts of the polymerizable materials in the premix. Examples are triethylene glycol-bis-acrylate, triethylene glycol bis-methacrylate, ethylene glycol-bis-acrylate, ethylene, glycol-bis-methacrylate, and methylene-bis-acrylamide. These multi-ethylenically unsaturated, free radically polymerizable materials crosslink the polymeric material. Other means of crosslinking include crosslinking the polymer with radiation, e.g., E-beam.

Polymerization of the premix is carried out using conventional methods, e.g. ultra-violet radiation, heat, E-beam and the like. Polymerization by ultra-violet radiation or heat is facilitated by the presence of a free radical initiator which is soluble in the polymerizable composition. The initiator is generally present in an amount of at least about 0.01 parts by weight per 100 parts of the polymerizable materials in the premix. Examples of useful thermal initiators are benzoyl peroxide, azobisisobutyronitrile, di-t-butyl peroxide, and cumyl peroxide. Examples of useful photoinitiators are disclosed in the article "Photoinitiators—An Overview" by G. Berner et al in the *Journal of Radiation Curing* (April, 1979) pp. 2 through 9. The preferred photoinitiator is benzildimethylketal.

It is often desirable to include a surfactant in the premix, preferably a silicone or fluorochemical surfactant. By doing so, the stability and density of the frothed premix are improved. These surfactants are not always necessary, but when used, are present, as shown in Table III, below, in amounts ranging from 0.5 to 6 parts by weight of the premix. Examples of useful surfactants are described in U.S. Pat. No. 4,415,615. A preferred fluorocarbon surfactant is available under the trade name FC 430, from the 3M Company.

Filler materials can also be incorporated in the premix prior to frothing and coating of the premix or during coating of the premix, the amount of filler being dependent upon the type of filler material being used and the properties desired. Useful filler materials include fibrous reinforcing strands, woven and nonwoven reinforcing fabrics, glass beads, plastic hollow microspheres or beads, viscosity-adjusting agents, pigments and absorbent particles. These may be used to enhance the internal strength of the adhesive film or to modify the adhesive and absorbent properties as shown in Example 22, below.

The pressure-sensitive adhesive films of the invention may be prepared by the methods disclosed in U.S. Pat. No. 4,415,615, the disclosure of which is incorporated herein by reference thereto. In general, the process involves the polymerization of a premix containing voids to a pressure-sensitive adhesive state by conventional means. The cellular voids area preferably formed in the premix before coating the premix onto a carrier. The premix can be coated by any suitable means, which will not destroy the cellular voids in the foamed premix.

Absorption capacity, conformability, MVT and cushioning may be controlled by varying the thickness of the adhesive film. Thickness of the adhesive film is determined by the dimensions of the aperture through which the frothed premix passes as it is being coated onto a carrier. Adhesive films having a thickness ranging from about 0.07 to about 1.7 mm are generally suitable. The minimum thickness of the adhesive film is dependent upon the maximum cell size generated in a particular film which is, in turn, determined by the processing conditions and chemical properties of the premix. For example, a surfactant-containing premix would result in an adhesive film with smaller cell diameters and could be coated thinner without the risk of discontinuities than a premix which does not contain surfactant. The maximum thickness is limited by the MVT desired and, as a practical matter, the amount of energy available to effect a complete cure.

An adhesive film of the present invention is preferably made by the sequential steps of:

(1) foaming a premix,
(2) coating the foamed premix onto a carrier, and
(3) polymerizing the coated premix in situ to a pressure-sensitive adhesive state.

Foaming of the premix is conveniently accomplished by whipping a gas, e.g. air, into the premix as disclosed in U.S. Pat. No. 4,415,615. Foaming of the premix could also be accomplished by including a blowing agent in the premix which can be volatilized to produce cellular voids in the adhesive.

Because the viscosity of a mixture of polymerizable monomers tends to be too low to provide a coatable froth or foam, several techniques have been used to thicken the mixtures before frothing or foaming, to provide a composition having a viscosity in the range of 1000 to 40,000 cps. One method is to add thickeners such as those described above to the polymerizable premix. Another method is to thicken the premix with a partially photopolymerized solution or syrup of isooctylacrylate (IOA) and acrylic acid (AA), or IOA and AA in polypropylene glycol.

After coating the foamed composition onto a substrate, the polymerization can be initiated by ultraviolet radiation as taught in U.S. Pat. No. 4,181,752. in situ polymerization can also be effected by electron beam. Because air tends to quench photopolymerization, the foaming gas is preferably inert, such as nitrogen or carbon dioxide.

When the polymerization is to be effected by ultraviolet radiation, the polymerizable coating is preferably protected from air by polymerization in an inert atmosphere or by the use of a plastic film overlay which is fairly transparent to ultraviolet radiation and has a low-adhesion surface. Biaxially-oriented polyethylene terephthalate film which is about 75% transparent to ultraviolet radiation is very useful as an overlay. If the underlying carrier also has a low-adhesion surface, both the carrier and the overlay can be stripped away so that the self-supporting adhesive film may be obtained.

Normally, one does not wish to have an unprotected film of the adhesive at this point in production. In practice, one may either retain the original carrier and overlay or replace one or both (e.g. by lamination) with a liner or backing more suitable for the product. For example, one may wish to use a release liner or a backing bearing a logo, a decorative design, or instructions for use of the product. Ideally, the carrier and the plastic film overlay have sufficiently attractive appearance and properties of low adhesion to the adhesive film that they can be used as protective liners for each face of the adhesive through converting operations and, most preferably, until the final product reaches the hands of the user. For example, when the pressure-sensitive adhesive film is to be used as a means of attaching an ostomy appliance to the skin of a patient, it is desirable to have easy-release liners on each face which are removed sequentially. For example, one might attach the first face of the adhesive to the skin and then an appliance to the second, exposed face of the adhesive.

When the adhesive film is used without a backing, it may be desirable to embed a layer of reinforcing material in the film to structurally support the film. This can be accomplished by coating a carrier with a layer of the polymerizable premix, laying down a layer of reinforcing material, e.g. a fabric, on the coating of premix and coating the exposed layer of reinforcing materials with another portion of polymerizable material. It may be necessary to polymerize the first coating of polymerizable premix before laying down and coating the layer of reinforcing material if the energy used to initiate polymerization radiates from a single source which is not sufficient to completely polymerize the premix throughout its entire thickness.

When making a wound dressing, one face (the skin-contacting side) of the adhesive film is covered with an easy-release liner, which is removed immediately prior to use, but the other face is usually covered with a backing, i.e., a material which reduces or eliminates the tack of that face of the adhesive and which is permanently attached to the adhesive layer. The backing must not reduce the MVT of the dressing below the required level. A number of materials are suitable for this purpose. For example, a coating of a finely divided inert solid, e.g., talc, or a microporous non-woven fabric or plastic film, e.g., polyethylene, polyvinylchloride, etc. can be used. A very thin continuous film (e.g. ca 25 micrometers) of polyurethane, e.g., Estane TM available from B. F. Goodrich, is preferred as a backing. This polyurethane is a polyoxyethylene polyurethane which contributes to the high MVT. This film has several advantages. It is very soft, and conforms well to body contours. It possesses high moisture vapor transmission (ca 1500 gm/m$^2$/hr), allowing absorbed water vapor to escape from the adhesive into the atmosphere. It is also impervious to bacteria.

For use, a dressing of this invention is attached to a patient's skin over a wound. In the normal healing process, aqueous fluid-bearing cells, etc. needed for wound repair, will ooze from the damaged tissue. When the wound is of considerable size, excess fluid may be produced. As a result of fluid production a significant pressure will build up in the wound cavity. As described above, the adhesive film already possesses a significant moisture vapor transmission (MVT), so that water vapor from the wound exudate will begin to penetrate the film. As it penetrates, it can encounter one or more of the small voids or reservoirs in the adhesive film. The effective thickness of the dressing as seen by molecules of water vapor passing through the dressing, is controlled by the number of reservoirs the molecules encounter, and by the thickness of the solid zones traversed by the molecules. It will be appreciated that the absorption capacity of the film is dependent upon both the diffusion of water molecules into the solid zones, and the capacity of the reservoirs to contain liquid water which has diffused into them as vapor. A film with only a relatively small number of reservoirs and relatively large solid zones between reservoirs would have a lower MVT than a low density, closed-cell foam adhesive film, in which the solid zones between the reservoirs are very small. A dressing of the latter type will have very high MVT relative to conventional dressings of comparable thickness. As a result, dressings of the present invention can provide optimum MVT previously obtainable only with films that are too thin and flimsy to handle easily.

There may be occasions when it would be desirable to include an extra, protective backing or embedded reinforcing layer, e.g., a fibrous and/or fabric filler as discussed above, when, for example, a dressing may be expected to be subjected to mechanical wear-and-tear. Such a backing or reinforcing layer need not be functional from the standpoint of controlling MVT, so long as it doesn't reduce the MVT of the dressing below the desired level. However, backing and reinforcing layers which affect MVT may be utilized to achieve the MVT properties desired in the dressing.

EXAMPLES

General Procedure For Frothing And Coating Adhesives

The uncured adhesive and surfactant solutions were pumped simultaneously using two Zenith QM1416 metering systems, one system at a 20:1 ratio and the other at a 30:1 ratio, (Fenner DC Controllers) and two Zenith gear pumps (BMC 5334 and BPB 5566) through a 99 mm single-stage mixer (SKG Industries) with introduction of nitrogen gas. The resulting frothed premix was coated between two low-adhesion carriers, at least one of which was transparent to UV radiation. The thickness of the coating was controlled by a nip roll or knife. The coating was irradiated through the transparent film(s) with 15 watt fluorescent black lights having a maximum at 350 nm. Conditions for frothing and coating were as follows unless otherwise noted.

| | |
|---|---|
| Uncured adhesive flow rate | 96 cc/min. |
| Surfactant flow rate | 4 cc/min. |
| $N_2$ flow rate | 100 cc/min. |
| Mixer Speed | 300 rpm |
| Back Pressure | 211 g/cm$^2$ |
| Adhesive Thickness | 0.760 mm |
| Exposure | $4 \times 10^6$ ergs |

Following the curing process, one of the low-adhesion carriers was removed and the adhesive was laminated onto a 0.025 mm thick, polyoxyethylene polyurethane film backing prepared as follows. A one mil, i.e., 25 micron film of Estane TM 58309-021 polyurethane resin (B. F. Goodrich, Cleveland, Ohio) was extruded using a three-quarter inch (1.9 cm) Rheomex Model 252 screw extruder (manufactured by Haake, Saddlebrook, N.J.), a sheeting die and a melt temperature of 190° C. The film was extruded onto the back clay-coated side of a 78 pound (35412 grams) paper which was clay-coated on one side by roll coating (No. 70-05-04-000, Boise Cascade Corporation, International Falls, Minn.). Immediately after extrusion the paper/resin combination was passed through a nip roll at 80 psi (5624 grams per square centimeter).

Premix Starting Materials

The following materials were used to prepare the adhesives shown in the following examples.

Thickeners

Thickener A. A solution composed of 30 parts of isooctylacrylate, 30 parts of acrylic acid, 40 parts of polypropylene glycol-425 (PPG-425, Dow Chemical), and 0.04 parts "Irgacure" 651 (2,2-dimethoxy-2-phenylacetophenone, Ciba Geigy) was simultaneously purged with nitrogen gas and irradiated with fluorescent black lights until a temperature of 79° C. was attained. The exposure was then stopped and the reaction was quenched with air. The resulting syrup had a viscosity of 11,000 cps at 25° C. and contained 75% residual acrylate monomer.

Thickener B. A solution containing 25 parts of isooctylacrylate, 25 parts of acrylic acid, 50 parts of polypropylene glycol 425 and 0.04 parts of "Irgacure" 651 was simultaneously purged with nitrogen gas and irradiated with fluorescent black lights until a temperature of 77° C. was attained. The irradiation was then stopped and the reaction was quenched with air. The resulting syrup had a viscosity of 6200 cps at 25° C. and contained 71% residual acrylate monomer.

Thickener C. A solution containing 80 parts of isooctylacrylate, 20 parts of acrylic acid and 0.04 parts of "Irgacure" 651 was purged with nitrogen and irradiated with fluorescent black lights. The resulting syrup had a viscosity of 11,000 cps at 25° C. and contained 89% residual monomer.

Thickener D. A solution containing 60 parts of glycerin and 40 parts of "Goodrite"K722 (a 37% aqueous solution of polyacrylic acid, MW 100,000, B. F. Goodrich) (PAA) was fed through a film extruder available from LUWA Co. at a rate of 100 lbs./hr., 160° F. and 5 mm Hg. The resulting syrup, consisting of 79.8% glycerin, 19.2% polyacrylic acid and 1.0% H₂O, had a viscosity of 200,000 cps at 25° C.

Thickener E. A solution containing 90 parts of isooctylacrylate, 10 parts of acrylic acid and 0.04 parts of "Irgacure" 651 was purged and irradiated as in C, above. The resulting syrup had a viscosity of 4330 cps at 25° C.

Thickener F. Sodium carboxymethyl cellulose, Type 7H, Hercules, Inc.

Thickener G. Polyvinylpyrrolidone K-90, GAF.

Thickener H. Low viscosity chitosan from Protan Laboratories, Inc.

Thickener I. A solution containing 80 parts of isooctylacrylate, 20 parts of acrylic acid and 0.04 parts of "Irgacure" 651 was simultaneously purged with nitrogen gas and irradiated with fluorescent black lights until a temperature of 67° C. was attained. The irradiation was then stopped and the reaction was quenched with air. The resulting syrup had a viscosity of 32,000 cps at 25° C.

Photoinitiators

Photoinitiator A: 2,2-dimethoxy-2-phenylacetophenone available as "Irgacure" 651 from Ciba-Geigy.

Photoinitiator B: hydroxycyclohexyl phenyl ketone available as "Irgacure" 184 from Ciba-Geigy.

Difunctional Monomers

TGBM: Triethylene glycol bis-methacrylate available from Sartomer Company.

EGBM: Ethylene glycol bis-methacrylate available from Sartomer Company.

Surfactants

Surfactant A. A solution of 70 parts of polypropylene glycol having a molecular weight of 425, 40 parts of a fluorosurfactant available as Fluorad ™ FC171 from 3M and 60 parts of a fluorosurfactant available as Fluorad ™ FC431 from 3M.

Surfactant B. A solution of 50 parts of polypropylene glycol 425 and 100 parts of a fluorosurfactant available as Fluorad ™ FC431 from 3M.

Surfactant C. A solution of 50 parts of polypropylene glycol-425 and 50 parts of a fluorosurfactant available as Fluorad ™ FC430 from 3M.

Surfactant D. A solution of 50 parts of polypropylene glycol-425 and 50 parts of a fluorosurfactant available as Fluorad ™ FC171 from 3M.

Surfactant E. To a solution of 60 parts of a fluorosurfactant available as Fluorad ™ FC431 from 3M and 40 parts of a fluorosurfactant available as Fluorad ™ FC171 from 3M was added 30 parts of carbitol acetate. Under reduced pressure, 30 parts of ethyl acetate were removed by distillation.

Test Methods

The tests used to evaluate the samples and generate the results shown in Table 4 were accomplished as follows.

Moisture Vapor Permeability

A modified Payne cup method is used. The method comprises the following steps:

(1) A 1⅜ inch (35 mm) diameter sample of material to be tested containing no perforations is cut.

(2) The sample is entered between the adhesive surfaces of two foil adhesive rings, each having a one inch (2.54 cm) diameter hole. The holes of each ring are carefully aligned. Finger presure is used to form a foil/sample/foil assembly that is flat, wrinkle-free and has no void areas in the exposed sample.

(3) A 4 ounce glass jar is filled half full of distilled water. The jar is fitted with a screw on cap having a 1.50 inch diameter hole in the center thereof and with a 1.75 inch diameter rubber washer having a 1.12 inch diameter hole in its center.

(4) The rubber washer is placed on the lip of the jar and the foil/sample assembly is placed on the rubber washer. The lid is then screwed loosely on the jar.

(5) The assembly is placed in a chamber at 100° F. (38° C.) and 20 percent relative humidity for four hours.

(6) The cap is tightened inside the chamber so the sample material is level with the cap (no bulging) and the rubber washer is in proper seating position.

(7) The assembly is removed from the chamber and weighed immediately to the nearest 0.01 gram (initial weight $-W_1$).

(8) The assembly is returned to the chamber for at least 18 additional hours.

(9) The assembly is removed from the chamber and weighed immediately to the nearest 0.01 gram (final weight $-W_2$).

(10) The water vapor transmission in grams of water vapor transmitted per square meter of sample area in 24 hours is calculated according to the following formula:

$$MVT = \frac{(W_1 - W_2) 4.74 \times 10^4}{T \text{(hours)}}$$

$W_1$ = initial weight (grams)
$W_2$ = final weight (grams)
$T^2$ = time (hours)

When a ⅛ inch sample is tested, the formula is changed to the following:

$$MVT = \frac{(W_1 - W_2) 1.9 \times 10^5}{T \text{(hours)}}$$

(11) Three samples of each material should be run and the average taken.

Absorbency

To determine absorbency, a sample of the cured adhesive was initially weighed and then immersed in deionized water at room temperature for one hour. The sample was then retrieved and weighed again. Absorbency is reported as the difference in weight divided by the initial weight. Optimal absorbency varies greatly depending upon the intended use of the adhesive film. For use on intact skin, low absorbencies are acceptable. Highly exudative wounds require higher absorbency films. Absorption capacity of the film can be controlled by the thickness of the film. In general, an absorbency of at least 50% over 1 hour is preferred.

180° Peel Adhesion

One inch (2.54 cm) wide test samples of the cured adhesive are self-adhered to the skin of a human volunteer under the weight of a 2.04-kg hard rubber roller, 2 passes in each direction. After 15 minutes dwell, 180° peel is measured by moving the free end of each tape away from the skin at a rate of about 0.5 cm per second (using a tensile tester). Samples were tested immediately after application (Initial) and at 6 hours after application (Final) and results reported. Preferred adhesives have an initial adhesion of at least about 5 g/cm, more preferably at least 10 g/cm and most preferably at least about 20 g/cm. The final adhesion is preferably less than double the initial adhesion.

Density

The density of the samples was measured by simply weighing a sheet of each sample and measuring the area and depth of the sheet to calculate volume.

EXAMPLES 1–5 and Comparative Example A

Examples 1–5 and Comparative Example A, summarized in Table I, below, were prepared by combining the thickener specified with additional isooctylacrylate ("IOA") and acrylic acid monomers ("AA") and polypropylene glycol ("PPG") to give the IOA:AA:PPG ratios (ratio includes copolymerized IOA and AA in thickener) and % solids (IOA-AA copolymer) indicated in Table I. "Irgacure" 651 was added at a level of 0.1% by weight. Triethylene glycol bis-methacrylate (TGBM) was added at the levels indicated and the mixture was mechanically stirred. The resulting solution was frothed in a 96:4 ratio with surfactant E, coated and cured as described in the "General Procedure".

TABLE I

Composition of Examples 1–5 and Comparative Example A

| Example | Monomer-Solvent Ratio | Thickener (wt. %) | Solids (wt. %) | TGBM (wt. %) | Thickness (mm) |
|---|---|---|---|---|---|
| 1 | IOA-AA-PPG 22.5-22.5-55 | A (69.3) | 10.4 | 2.9 | 0.76 |
| 2 | IOA-AA-PPG 22.5-22.5-55 | A (69.3) | 10.4 | 2.9 | 0.25 |
| 3 | IOA-AA-PPG 40-20-40 | C (50) | 7.3 | 1.5 | 0.76 |
| 4 | IOA-AA-PPG 35-25-40 | C (44) | 6.4 | 2.0 | 0.76 |
| 5 | IOA-AA-PPG 40-20-40 | C (50) | 7.3 | 2.0 | 0.76 |
| A | IOA-AA 90-10 | E (100) | — | — | 0.76 |

EXAMPLES 6–18

Examples 6–18 were prepared by combining thickener D [an 80/20 glycerin-polyacrylic acid ("PAA") solution] with acrylic acid and glycerin to give the AA:glycerin:PAA ratio indicated in Table II. To this was added "Irgacure" 651 at a level of 0.1%, difunctional monomer TGBM or EGBM, and, optionally, lithium hydroxide as indicated, and the mixture was mechanically stirred. The resulting solution was frothed in combination with the surfactant indicated, coated and cured according to the "General Procedure".

TABLE II

Composition of Examples 6–18

| Ex. No. | AA (wt. %) | Glycerin (wt. %) | PAA (wt. %) | Difunctional Monomer (wt. %) | LiOH (wt. %) | Surfactant (wt. %) | Thickness (mm) |
|---|---|---|---|---|---|---|---|
| 6 | 25 | 67.5 | 7.5 | TGBM (0.2) | — | E (4) | .762 |
| 7 | 25 | 67.5 | 7.5 | TGBM (0.2) | — | E (4) | .330 |
| 8 | 25 | 67.5 | 7.5 | TGBM (0.2) | — | E (4) | .127 |

TABLE II-continued

Composition of Examples 6-18

| Ex. No. | AA (wt. %) | Glycerin (wt. %) | PAA (wt. %) | Difunctional Monomer (wt. %) | LiOH (wt. %) | Surfactant (wt. %) | Thickness (mm) |
|---|---|---|---|---|---|---|---|
| 9 | 30 | 60 | 10 | TGBM (0.3) | — | E (4) | .762 |
| 10 | 25 | 67.5 | 7.5 | TGBM (0.2) | — | C (4) | .762 |
| 11 | 25 | 67.5 | 7.5 | TGBM (0.2) | — | C (2) | .762 |
| 12 | 25 | 67.5 | 7.5 | TGBM (0.2) | — | C (1) | .762 |
| 13 | 25 | 67.5 | 7.5 | TGBM (0.2) | — | none | .762 |
| 14 | 25 | 67.5 | 7.5 | TGBM (0.2) | — | D (4) | .762 |
| 15 | 25 | 67.5 | 7.5 | TGBM (0.2) | — | A (4) | .762 |
| 16 | 25 | 67.5 | 7.5 | TGBM (0.2) | — | B (4) | .762 |
| 17 | 19.4 | 68.4 | 5.9 | TGBM (0.2) | 5.9 | E (3) | .762 |
| 18 | 19.4 | 68.4 | 5.9 | EGBM (0.2) | 5.9 | E (4) | .762 |

Examples 11 and 12 were the same as Example 10 with the exception that the level of surfactant was varied. In Example 13, no surfactant was used. The absence of an effect from these variations upon the foamed density is shown in Table III.

TABLE III

Foam Density of Examples 10-13

| Example | Surfactant C (wt. %) | Foam Density (g/cc) |
|---|---|---|
| 10 | 4 | 0.51 |
| 11 | 2 | 0.53 |
| 12 | 1 | 0.51 |
| 13 | 0 | 0.53 |

EXAMPLE 19

To 1500 g of the uncured adhesive solution described in Example 6 was added 105 g of glass bubbles (Product #B-22-AS, 3M) with mechanical stirring. The suspension was frothed in 96:4 ratio with surfactant E, coated and cured according to the general procedure.

EXAMPLE 20

To 900 g of the uncured adhesive solution described in Example 6 was added 63 g cross-linked polyvinylpyrrolidone (#85,648-7, Aldrich Chemical Company) with mechanical stirring. The resulting suspension was frothed, coated and cured according to the "General Procedure" in a 96:4 ratio with surfactant E.

EXAMPLE 21

To a mechanically stirred solution of 875 g of glycerin, 375 g of $H_2O$, 500 g of acrylic acid, 120 g of lithium hydroxide, 6.0 g of triethylene glycol bis-methacrylate, 1.0 g of Irgacure 651 and 1.0 g of methyl hydroquinone, an antioxidant hereinafter referred to as MEHQ, was added 50 g of sodium carboxymethyl cellulose (Type 7H, Hercules). The resulting solution having a viscosity of 6500 cps at 25° C. was frothed, coated and cured according to the General Procedure in a 96:4 ratio with surfactant E.

EXAMPLE 22

To a mechanically stirred solution of 720 g of glycerin, 720 g of $H_2O$, 400 g of acrylic acid, 2.0 g of Irgacure 184, 120 g of lithium hydroxide and 1.0 g of MEHQ was added 60 g of low viscosity chitosan (Protan Laboratories, Inc.). The resulting solution having a viscosity of 2000 cps was frothed, coated and cured according to the "General Procedure" in a 96:4 ratio with surfactant E.

EXAMPLE 23

The uncured adhesive solution described in Example 14 was frothed according to the "General Procedure" in a 96:4 ratio with surfactant E and was coated in two 0.015" layers with a spun-bonded nylon fabric (1.0 oz., Cerex) sandwiched between the layers. The resulting multi-layer coating was cured according to the "General Procedure".

The properties of the adhesives prepared in Examples 1-23 and Comparative Example A are shown in Table IV, below.

TABLE IV

Properties of Dressings with Backings

| Ex. No. | Foamed | | Unfoamed | | 180° Peel Adhesion | | Density (g/cc) | Void Volume (Percent) |
|---|---|---|---|---|---|---|---|---|
| | MVT ($g/m^2$ - 24 h) | Absorbency (Percent) | MVT ($g/m^2$ - 24 h) | Absorbency (Percent) | Initial (g/cm) | Final (g/cm) | | |
| 1 | 477 | 13.2 | 316 | — | 27.5 | 36.6 | 0.915 | 15 |
| 2 | 411 | 10.0 | 283 | 7.9 | 34.6 | 49.2 | 0.903 | 17 |
| 3 | 299 | 17.5 | 141 | 4 | 27.6 | 21.6 | 0.946 | 12 |
| 4 | 266 | 13 | 166 | 9 | 20.9 | 19.7 | 0.952 | 14 |
| 5 | 291 | 17 | 183 | 5.7 | — | — | 0.671 | 67 |
| A | 207 | 21 | 102 | 19 | 41.3 | 116 | — | 42 |
| 6 | 921 | 1478 | 859 | 788 | 98.4 | 70.9 | 1.007 | 23.6 |
| 7 | 1198 | 6977 | 1059 | 4323 | 88.6 | 74 | 1.129 | 7.4 |
| 8 | 1179 | 9926 | 1202 | 6085 | 35.4 | 59.1 | — | — |
| 9 | 1223 | 1519 | 1141 | 734 | 7.1 | 17.7 | 1.129 | 13 |
| 10 | 1339 | 1023 | 1226 | — | 88.6 | 82.6 | 1.025 | 21.5 |
| 14 | 1271 | 1259 | 1388 | — | 72.8 | 87.4 | 1.068 | 18.3 |
| 15 | 1405 | 1651 | 1257 | — | 74.8 | 69.7 | 1.019 | 21.7 |
| 16 | 1315 | 1191 | 1285 | — | 66.9 | 71.7 | 0.995 | 23.7 |
| 17 | 1249 | 1837 | 1016 | 3601 | 88.9 | 118.7 | — | — |
| 18 | 1083 | 4016 | 1029 | 4641 | 49.4 | 43.7 | — | — |
| 19 | 1264 | 1937 | 936 | 908 | 54.3 | 88.6 | 0.84 | 15.4 |
| 20 | 1090 | 459 | 1032 | 427 | 44.5 | 61.0 | 1.03 | 18.6 |

TABLE IV-continued

| | Properties of Dressings with Backings | | | | | | | |
|---|---|---|---|---|---|---|---|---|
| | Foamed | | Unfoamed | | 180° Peel Adhesion | | | Void |
| Ex. No. | MVT (g/m² - 24 h) | Absorbency (Percent) | MVT (g/m² - 24 h) | Absorbency (Percent) | Initial (g/cm) | Final (g/cm) | Density (g/cc) | Volume (Percent) |
| 21 | 1194 | 6383 | 1215 | 5379 | 0.98 | 9.06 | 1.08 | 14.6 |
| 22 | 1266 | dissolved | 1074 | dissolved | 7.3 | 12.4 | 0.616 | 45.2 |
| 23 | 1125 | 312 | 899 | 262 | 70.1 | 68.9 | 1.09 | 15.0 |

EXAMPLE 24

A sample was prepared as described in Example 6 with the following modification. During the coating process, the froth was coated directly onto the 0.01 inch thick polyurethane backing film described in the "General Procedure", and covered with a transparent low-adhesion liner. The General Procedure for curing provided a foamed adhesive with a polyurethane backing on a low-release liner. In this case, the additional step of laminating a backing to the cured adhesive was eliminated.

EXAMPLE 25

A foamed pressure-sensitive adhesive in which the hydrophilizing component is covalently bonded into the polymer network can be prepared by the following procedure: To a solution of 300 g of Thickener I, 100 g of acrylic acid, 5.0 g of TGBM and 2 g of Irgacure 651, add 600 g of a polyoxyalkyleneacrylate. (A polyoxyalkyleneacrylate can be obtained by adding dropwise, 155 g of 2-isocyanatoethylmethacrylate to a nitrogen purged solution of 4 drops of dibutyltindilaurate and 2170 g of an amine-functional poly(alkylene oxide) having the formula $(CH_3OCH_2CH_2O(CH_2CH_2O)_n(CH_2(CH_3)CHO)_mCH_2(CH_3)CHNH_2$ where $n/m=2/32$, (available as Jeffamine M-2005 from the Texaco Chemical Company), and heating to 35° C. for 2 hours.) The resulting adhesive premix solution is frothed, coated and cured and the resulting film is laminated to a 0.025 mm polyurethane film as described in the General Procedure.

EXAMPLES 26–31

In Examples 26–31, earlier examples were repeated with the exception that a different backing or no backing was used when the MVT of the adhesive was tested.

EXAMPLE 26

A sample was prepared as described in Example 6 except that the backing lamination step was omitted. The final product consisted of a foamed adhesive layer between two low-adhesion liners. Removal of both liner films at the time of application provided a dressing which was tacky on two sides and was suitable for attachment of additional devices such as an ostomy or exudate collective device.

EXAMPLE 27

A sample was prepared as in Example 6, except a rayon non-woven web as described in U.S. Pat. No. 3,121,021 to Copeland, the backing used in Micropore TM brand tape (3M), was substituted for the polyurethane film in the backing lamination step.

EXAMPLE 28

A sample was prepared as described in Example 3 except that the backing lamination step was omitted.

EXAMPLE 29

A sample was prepared as described in Example 4 except that the backing lamination step was omitted.

EXAMPLE 30

A sample was prepared as described in Example 1 except that the backing lamination step was omitted.

COMPARATIVE EXAMPLE B

A sample was prepared as described in Comparative Example A above, except that the backing lamination step was omitted.

TABLE V

| | Effect of Backing on MVT | | |
|---|---|---|---|
| Example | IOA/AA/PPG | Backing* | MVT (g/m² - 24 hr) |
| 6 | — | I | 921 |
| 26 | — | none | 3476 |
| 27 | — | II | 3219 |
| 3 | 40/20/40 | I | 299 |
| 28 | 40/20/40 | none | 447 |
| 4 | 35/25/40 | I | 266 |
| 29 | 35/25/40 | none | 566 |
| 1 | 22.5/22.5/55 | I | 477 |
| 30 | 22.5/22.5/55 | none | 531 |
| A | 90/10/0 | I | 207 |
| B | 90/10/0 | none | 329 |

*Backings:
I: 0.025 mm polyurethane film
II: non-woven rayon web

The data shown in Table V illustrate the general superiority, in terms of MVT, of the adhesives of this invention as compared with adhesives of the type shown in Comparative Examples A and B.

EXAMPLE 31

In order to confirm the impermeability to liquid water, the adhesive described in Example 23 was evaluated by the following procedure. The apparatus used consisted of a pressure loop made of copper tubing, 4.13 cm in diameter One end of the loop was connected to a source of compressed air and was fitted with a pressure regulator. The opposite end of the loop had a flat rigid flange of 7.6 outer diameter and 3.6 cm inner diameter with a rubber O-ring of 4.4 cm diameter embedded in the flange for sealing. A matching top ring was used to clamp the test samples in place.

The pressure loop was fitted with a solution of 692 parts deionized water, 7 parts DOWFAX TM 2A1 surfactant available from Dow Chemical Co., and 0.7 parts methylene blue dye. The adhesive sample with both low-adhesion carriers removed, was laminated to a single layer of Whatman 4-Qualitative filter paper. With the filter paper side facing away from the dye solution, the test sample was secured between the two flanges of the apparatus described above, and the apparatus was rotated to exclude air between the sample and the dye solution. Air pressure of 76.2 cm of water was applied for two minutes at which time no evidence of dye solution wetting the paper was observed. The air pressure was increased until the filter paper split due to expansion of the adhesive; still no evidence of wetting of the paper was observed which indicated that the foamed adhesive sample was not permeable to liquid water.

What is claimed is:

1. A method of treating a wound comprising covering the wound with a dressing comprising a hydrophilic film of pressure sensitive adhesive, which film is continuous and liquid impermeable over its entire surface, said film having dispersed therein cellular voids containing a gaseous phase constituting at least 10 percent of the volume of said film, and a 0.76 mm thickness of said film having a moisture vapor transmission rate of at least about 400 g/m$^2$ per 24 hours at 40° C. and an 80 percent humidity differential.

2. A method of attaching a device or article to the skin comprising attaching said device or article to the skin with a pressure sensitive adhesive wherein said adhesive comprises a hydrophilic film which is continuous and liquid impermeable over its entire surface, said film having dispersed therein cellular voids containing a gaseous phase constituting at least 10 percent of the volume of said film, and a 0.76 mm thickness of said film having a moisture vapor transmission rate of at least about 400 g/m$^2$ per 24 hours at 40° C. and an 80 percent humidity differential.

3. The method according to claim 1 wherein the hydrophilic film is comprised of a hydrophilizing agent selected from the group consisting of polyhydric polyols, polyethers and mixtures thereof.

4. The method according to claim 3 wherein the hydrophilizing agent is glycerin.

5. The method according to claim 1 wherein the film is comprised of a polymer comprised of repeating units derived from the polymerization of at least one ethylenically unsaturated monomer selected from the group consisting of alkyl acrylates having an average of 4–12 carbon atoms in their alkyl groups, acrylic acid, methacrylic acids, and salts thereof, acrylamide, methacrylamide, hydroxyalkylacrylates, hydroxyalkylmethacrylates, acrylonitrile, methacrylonitrile, cyanoethylacrylate, maleic anhydride and N-vinyl-pyrrolidone.

6. The method according to claim 5 wherein the ethylenically unsaturated monomer is further comprised of one or more monomer units derived from a polyether terminated with an ethylenically unsaturated group.

7. The method according to claim 6 wherein the polyether is an acrylate-terminated polyethylene oxide.

8. The method according to claim 6 wherein the polyether is an acrylamide-terminated polypropylene oxide.

9. The method according to claim 1 wherein the film is from about 0.07 mm to about 1.7 mm in thickness.

10. The method according to claim 1 wherein the film has a void volume of from about 10 percent to about 85 percent.

11. The method according to claim 1 wherein the film further comprises a reinforcing layer embedded therein.

12. The method according to claim 11 wherein the reinforcing layer is a fabric.

13. The method according to claim 1 further comprising a backing covering one face of the film.

14. The method according to claim 13 wherein the backing is a comfomable sheet having a moisture vapor transmission rate of at least about 1000 g/m$^2$ per 24 hours measured at 40° C. and 80% relative humidity differential.

15. The method according to claim 1 wherein said film has an absorbency of at least 50% over one hour.

16. The method according to claim 1 wherein a 0.76 mm thickness of said film has a moisture vapor transmission rate from about 600 to about 2400 g/m$^2$ per 24 hours at 40° C. and an 80% humidity differential.

17. The method according to claim 2 wherein said film is comprised of a copolymer comprised of repeating units derived from a polyether terminated with an ethylenically unsaturated group.

18. The method according to claim 2 wherein the film is from about 0.07 mm to about 1.7 mm in thickness.

19. The method according to claim 2 wherein the film has a void volume of from about 10 percent to about 85 percent.

20. The method according to claim 2 wherein the film further comprises a reinforcing layer embedded therein.

21. The method according to claim 2 further comprising a backing covering one face of the film.

22. The method according to claim 2 wherein said film has an absorbency of at least 50% over one hour.

23. The method according to claim 2 wherein a 0.76 mm thickness of said film has a moisture vapor transmission rate from about 600 to about 2400 g/m$^2$ per 24 hours at 40° C. and an 80% humidity differential.

* * * * *

UNITED STATES PATENT AND TRADEMARK OFFICE
CERTIFICATE OF CORRECTION

PATENT NO. :   5,009,224
DATED      :   April 23, 1991
INVENTOR(S) :  Susan M. Cole It is certified that error appears in the above-identified patent and that said Letters Patent is hereby corrected as shown below:

Col. 6, line 57, "in situ" should read --In situ--.
Col. 18, line 31, "copolymer" should read --polymer--.

Signed and Sealed this

Twentieth Day of July, 1993

Attest:

MICHAEL K. KIRK

Attesting Officer

Acting Commissioner of Patents and Trademarks